United States Patent [19]
Bondi et al.

[11] Patent Number: 4,752,478
[45] Date of Patent: Jun. 21, 1988

[54] TRANSDERMAL SYSTEM FOR TIMOLOL

[75] Inventors: Joseph V. Bondi, Collegeville; Alice E. Loper, Harlseyville; Edward M. Cohen, Norristown, all of Pa.

[73] Assignee: Merck & Co., Inc., Rahway, N.J.

[21] Appl. No.: 682,447

[22] Filed: Dec. 17, 1984

[51] Int. Cl.$^4$ .................. A61L 15/03; A61F 13/00; A61K 9/70
[52] U.S. Cl. .................................. 424/449; 424/448
[58] Field of Search .................. 604/897, 896, 897; 424/28, 449

[56] References Cited

U.S. PATENT DOCUMENTS

| | | | |
|---|---|---|---|
| 3,598,122 | 8/1971 | Zaffaroni | 604/897 |
| 3,797,494 | 3/1974 | Zaffaroni | 604/897 |
| 4,031,894 | 6/1977 | Urquhart et al. | 128/268 |
| 4,060,084 | 11/1977 | Chandrasekaran et al. | 128/260 |
| 4,286,592 | 9/1981 | Chandrasekaran | 804/897 |
| 4,420,470 | 12/1983 | Otsuka et al. | 424/28 |
| 4,421,737 | 12/1983 | Ito et al. | 424/28 |
| 4,428,883 | 1/1984 | Hussain | 424/248.51 |
| 4,440,777 | 4/1984 | Zupan | 424/274 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,478,822 | 10/1984 | Haslam et al. | 424/78 |
| 4,483,846 | 11/1984 | Korde et al. | 424/28 |
| 4,559,222 | 12/1985 | Enscore et al. | 424/28 |
| 4,560,553 | 12/1985 | Zupan | 424/78 |

OTHER PUBLICATIONS

Chemical Abstracts: 100:180132j, Transdermal Pharmaceutical Tapes Containing Aluminum Hydroxide, Sodium Salt of Acrylic Polymers.

Chemical Abstracts: 101:12230s, Transdermal Tapes Containing Propranolol.

Goodman & Gilman, Pharmacological Basis of Therapeutics, pp. 195-196, 6th Edition, MacMillan Publishing.

*Primary Examiner*—Shep K. Rose
*Attorney, Agent, or Firm*—Alice O. Robertson; Michael C. Sudol

[57] ABSTRACT

A method and device for administering timolol for an extended period is described. By the method and device, transdermal application of timolol may be accomplished with substantially no irritation to the skin.

20 Claims, 1 Drawing Sheet

TRANSDERMAL SYSTEM FOR TIMOLOL

The present invention relates to transdermal application of timolol, more particularly to a method and device for application over an extended period of time with a minimal amount of the undesirable side effect of irritation and/or erythema of the skin.

BACKGROUND OF THE INVENTION

Transdermal methods have been devised for administering controlled quantities of systemically active drugs. However, to be useful, the drug must be permeable through the skin. Even if permeable, the method may still not be useful because of irritation caused to the skin. This is especially important with certain drugs in which the continuous supplying of a therapeutic drug over an extended period of time is highly desirable. Unfortunately, some drugs such as timolol while adaptable to therapy via a transdermal system by virtue of being absorbable through the skin, heretofore have not been adaptable to long term therapy because of the irritation caused to the skin. By "extended period" as herein employed is meant time which is long enough to be measured in numbers of days.

STATEMENT OF THE INVENTION

According to the present invention it has been discovered that the drug timolol may be administered transdermally over an extended period to obtain efficient beta blockade with substantially no irritation or very minimal irritation to the skin by supplying said timolol at a controlled low zero order rate. By employing an appropriate controlled rate of delivery to the skin, it has been found that therapeutic doses of timolol may be supplied over an extended period of time.

DESCRIPTION OF THE INVENTION

There has been discovered a method of administering timolol transdermally over an extended period with substantially no irritation to the skin by supplying timolol at a zero order rate of not greater than 20 micrograms per square centimeter per hour (20 mcg/cm$^2$/hr). A useful range is in the order of from about 7 mcg/cm$^2$/hr to about 15 mcg/cm$^2$/hr, with a preferred range of from about 7 mcg/cm$^2$/hr to about 13 mcg/cm$^2$/hr with about 12 mcg/cm$^2$/hr being most preferred. The lower range for administration accommodates patients with high dermal sensitivity. When the preferred rates are employed, it has been found that there is minimal irritation and by adjusting the size of the patch to provide the amount necessary for the essential therapeutic dose, an excellent complete β-blockade can be achieved, as can be seen, for example, in a significant reduction in exercise heart rate.

The method of the present invention is most readily carried out by means of a transdermal delivery system and the patch or bandage through which it is effected and which comprises an aspect of the present invention. As herein employed the expression "transdermal delivery system" is employed to refer to the essential components for carrying out the present invention, namely, the backing member, the drug reservoir and the rate-controlling member. By the expression "transdermal patch" or "transdermal bandage" is meant the transdermal delivery system plus a means to attach the system to the skin. The transdermal system and transdermal patch are described with reference to the drawings.

FIGS. 1a, 1b, 1c, 1d and 1e are fragmentary enlarged cross-sectional views of several embodiments of component elements of a transdermal delivery system.

Figure 1:
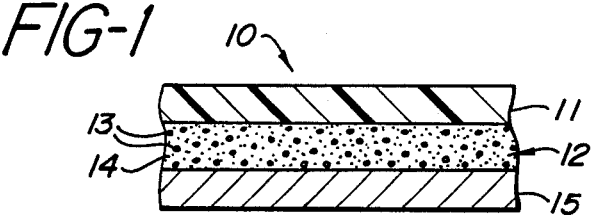
FIG. 1 is a fragmentary enlarged cross-sectional view depicting the essential component elements of a transdermal delivery system of a transdermal patch.
Figure 1:
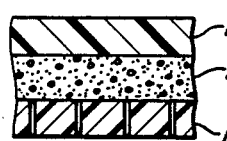
Figure 1:
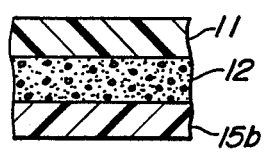
Figure 1:
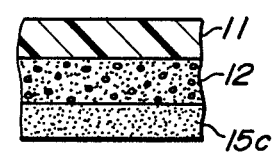
Figure 1:
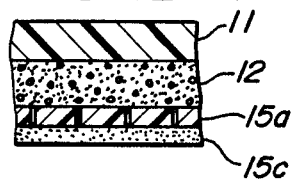
Figure 1:
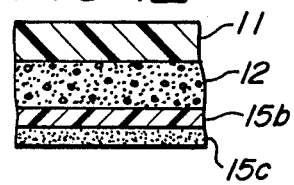

Referring to the drawings, there is shown a transdermal delivery system 10 which comprises an impermeable backing member 11, a drug reservoir member 12 consisting of the drug, 13 dispersed in carrier 14, and a rate controlling member 15, said system which together with a means to attach the system to the skin forms a transdermal patch or bandage. The rate controlling member may be (a) a microporous membrane 15a as seen in FIG. 1a, (b) a diffusion controlling membrane 15b as seen in FIG. 1b, (c) a rate controlling adhesive as seen in FIG. 1c, (d) a combination of a microporous membrane 15a and an adhesive layer having rate controlling properties 15c which together perform the rate controlling function as seen in FIG. 1d, or (e) may be a combination of a diffusion controlling membrane 15b and a rate controlling adhesive layer 15c as seen in FIG. 1e. When an adhesive is contributing to or performing a rate controlling function, the adhesive in these instances is performing a dual function of rate control and of attaching the transdermal delivery system to the skin.

Figure 2:
FIG. 2 is a cross-sectional view illustrating one embodiment of a transdermal patch.
Figure 3:
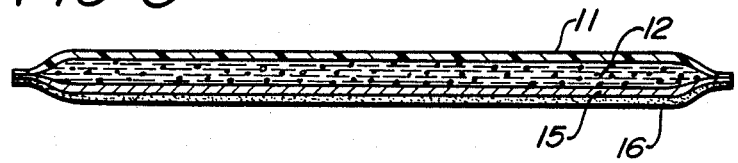
FIG. 3 is a cross-sectional view illustrating another embodiment a transdermal patch.

FIG. 2 depicts an embodiment of a transdermal patch in which the drug reservoir is a solid. FIG. 3 depicts an embodiment in which the drug reservoir is a semisolid or ointment wherein the face of the backing member contiguous to the drug reservoir is joined at the edges to the face of the microporous membrane contiguous to the drug reservoir. The edges are joined preferably by heat-sealing, but also may be sealed by crimping, using sealants, and by other means for effecting a seal.

The impermeable backing member 11 is preferably of a polyester occlusive film. Other materials suitable for a backing include foil, polyethylene coated foil, polyethylene, Mylar polyester, polypropylene and the like.

The drug reservoir is a dispersion of timolol in a carrier. The carrier may be a solid, i.e., of a non-mobile or non-flowable material or may be of a semi-solid preparation often referred to as ointments. Suitable semisolid carriers include gelled mineral oil e.g., mineral oil gelled with 5 percent polyethylene (commercially available as Plexi Gel 50W from Parke Davis), polyisobutylene, aluminum stearate, or even propylene glycol, or fatty acid esters. Solid carriers include silicone, acrylic adhesive, plasticized polyvinyl chloride, and the like. By "drug reservoir composition" is meant timolol in one of the aforementioned carriers.

Membrane 15a, a microporous membrane, may be of any porous material permitting the passage of the drug and is inclusive of microporous polypropylene, microporous nylon, microporous polycarbonate and the like. The membrane layer may be a single layer or may be of multiple layers of selected microporous materials which have been laminated together. The drug passes through the micropores which are filled with mineral oil or other carrier material during fabrication. The control effected by the membrane is not by the dissolution of the drug in the membrane material but merely in travel through the pores.

Membrane 15b, a diffusion controlling membrane, may be of (materials in which the timolol dissolves and is inclusive of silicone, ethylene vinyl acetate and polyurethane.

When the rate controlling member is an adhesive rate controlling member 15c, the preferred adhesive is selected from a class of rubber based adhesives. Other adhesives include suitable medical grade adhesive which permits migration. Examples of such adhesives include polymers of esters with acrylic acid, copolymers of the esters with other acrylic derivatives such as acrylic acids, acrylamides, elastomeric silicone polymers, vinyl polymers such as polyvinyl alcohols, polyvinylpyrrolidones, polyvinyl acetates, blends of cellulose derivatives and natural gums such as guar gum, pectin and the like. When the adhesive is to be employed solely as attachment means for a patch, an adhesive having no rate-controlling properties is employed. Generally, such adhesives are acrylate based adhesive systems.

The rate of travel of the drug is controlled by several factors, the porosity or diffusion coefficient of the drug in the membrane, thickness of the membrane or the rate controlling adhesive, and the solubility of the drug in the carrier material of the drug reservoir.

The size of the patch depends on the required surface area of the drug which in turn depends on the amount of drug which must be delivered employing a rate of delivery which is no greater than about 20 mcg/cm$^2$/hr. Generally, a suitable patch can be fabricated in the size range of about 13 to about 30 square centimeters. A smaller patch would usually necessitate a higher rate of delivery thereby rendering the use likely to be accompanied by irritation. A larger patch would be undesirable from the standpoint of inconvenience to the patient to wear such a large device. By proper selection of size and delivery rate, a patch can be found which is suitable for supplying the necessary therapeutic dose while accomodating to the patient's particular skin sensitivity.

The transdermal patch may be fabricated by uniformly applying a drug reservoir composition to a backing member, thereafter applying a rate-controlling member, and if necessary, i.e., when rate-controlling member is a membrane and nonadhesive, applying an adhesive composition. If the drug reservoir is semisolid, then a membrane must be employed and the membrane must be sealed to the backing layer before applying the adhesive. After application of the adhesive, the bandage may be cut to the desired size. It is to be understood that in the preferred article of the present invention, an adhesive layer is the means for attaching the bandage to the skin. However, a separate bandage material may be employed to attach the transdermal delivery system of the present invention to the skin.

Thus, initially a selection is made of the drug reservoir composition and the rate controlling member, and the determination of flux is made in vitro. For the determination of flux, a dispersion of timolol in the selected carrier is placed behind the selected membrane material in a diffusion cell and rate of release into an isotonic phosphate buffer is determined. If a constant rate of release into a perfect sink is obtained, i.e., no accumulation occurring after passage across the membrane, the measured flux may be described according to the following equation:

$$J = \frac{E \cdot D \cdot K_p \cdot C_s}{h}$$

If the membrane is a porous membrane, E is membrane porosity, D is the diffusion coefficient of the drug through the reservoir material, $K_p$ is 1, $C_s$ is the drug concentration in the reservoir and h is the membrane thickness. If the membrane is a non-porous diffusion controlling membrane, E is 1, D is the diffusion coefficient of the drug in the membrane, $C_s$ is the solubility of the drug in the reservoir and $K_p$ is the partition coefficient between the drug in the membrane and the drug in the reservoir.

Thus, for a given reservoir and membrane of known porosity or diffusion coefficient with respect to drug and thickness, flux can be determined experimentally. Since $D \cdot K_p$ which can be calculated from the above relationship will be constant for the same reservoir material and membrane, it is evident from the equation that the flux can be changed by modifying the thickness of the membrane. Depending on the rate desired, this can be accomplished by employing multiple thicknesses. Thus, to decrease the flux to one third, a triple thickness of the membrane would be employed. When the rate controlling member is an adhesive layer, flux can be determined in a similar way after initially forming an adhesive layer by casting an adhesive composition onto a release liner, then drying to form an adhesive layer which then may perform as a membrane. After determination of the relation of flux to a particular thickness of adhesive, controlled application of adhesive of the desired thickness may be employed in manufacture. Alternatively, an adhesive having the desired thickness may be manufactured separately and applied by laminating methods known in the art.

For other modifications, a combination of membranes may be employed. When different membranes are employed, the relationship among the resistance offered by the individual membranes and the net resistance may be represented by the formula:

$$\frac{1}{J_{net}} = \frac{1}{J_1} + \frac{1}{J_2}$$

where $J_1$ and $J_2$ are flux values for membranes 1 and 2. Thus, if a layer of membrane 1 and a layer of membrane 2 are employed, the resulting membrane would have flux represented $J_{net}$ obtained by calculation. Conversely, desiring a particular flux, the selection of a second membrane to be employed with the one already at hand can be accomplished readily. Thus, by combining membranes of different porosity, any desired flux may be readily attained.

The following examples illustrate the invention but are not to be construed as limiting:

EXAMPLE I

A. Preparation of Patches

Transdermal timolol patches of 10 centimeters square in size, containing timolol in gelled mineral oil and designed to deliver approximately 32, 13.5 and 6.7 micrograms per square centimeter per hour (mcg/cm$^2$/hr) through a microporous membrane were prepared.

As a first step in the preparation of the patches, commercially available membrane materials of known porosity and thickness were employed to determine the release rates for timolol through a single layer of each membrane into an isotonic phosphate buffer and to calculate the necessary combination of membranes to provide appropriate delivery rates. Commercial microporous polypropylene membrane (sold by Celanese Corporation under the tradename Celgard 2402) of a thickness of 0.005 centimeter and a porosity of 38 percent was found experimentally to have a flux of 40 mcg/cm²/hr. The concentration of timolol hemihydrate in solution in gelled mineral oil had previously been determined to be 7000 mcg/ml in the presence of excess solid. Substituting these figures in the equation $$J = \frac{EDK_p C_s}{h}$$

for measured flux, the term $D K_p$ was calculated to for measured be $7.5 \times 10^{-5}$ cm/hr which would be constant for the membrane. By appropriate substitution, a membrane having a flux of approximately 13.5 mcg/cm²/hr was determined to be one having three thicknesses of the membrane and a membrane having a flux of approximately 6.7 mcg/cm²/hr was determined to be one having six thicknesses of said membrane (Celgard 2402).

In a similar manner, commercial microporous polypropylene membrane having a thickness of 0.0025 centimeter and a porosity of 45 percent (Celgard 2500) was determined experimentally to have a flux of 160 mcg/cm2/hr. By substituting the fluxes of the two membranes into the equation:

$$\frac{1}{J_{net}} = \frac{1}{J_1} + \frac{1}{J_2}$$

the $J_{net}$ was found to be 35 mcg/cm²/hr. Thus, by using one layer of Celgard 2402 and one layer of Celgard 2500, a membrane having a flux of about 32 mcg/cm²/hr was provided.

The patches then were prepared by (a) applying to each 10 centimeter square of polyester coated aluminum foil backing material, approximately 250 milligram portions of 40 percent (weight/weight) timolol ointment (timolol hemihydrate in a commercial gelled mineral oil of 5 percent polyethylene in heavy mineral oil), (b) placing the appropriate previously determined membrane on the timolol ointment, (c) applying pressure to uniformly spread the ointment constituting the drug reservoir between the backing and the membrane and (d) heat sealing the edges and cutting when necessary to a uniform size. In addition to the foregoing, a placebo patch was prepared of gelled mineral oil for the drug reservoir and one layer of Celgard 2402 and one layer of Celgard 2500 for the membrane.

The actual in vitro delivery rates of the patches were determined by the U.S.P. Paddle Method. The Paddle Method determination is an U.V. detection of released material. In this case, the timolol (as a free base) was released from the patches when the patches were subjected to pH 7.4 in isotonic phosphate buffer. In the determination, the patches were placed in the buffer solution in flasks fitted with paddles set 8 centimeters from the bottom and agitated at 32° C. Samples were withdrawn over a seven day period and absorbance determined and compared with standard timolol solution at 294 nm. The amount of timolol free base released from the patch was determined according to the formula:

$$\text{Amount} = \frac{Au}{As} \times Ws \times \frac{Du}{Ds} \times 0.732 \times \frac{P}{100}$$

where Au is UV absorbance of sample at 294 nm, As is absorbance of a timolol maleate standard at 294 nm, Ws is weight of timolol maleate standard (milligrams), Du is dilution factor for sample, 0.732 is conversion factor from timolol maleate to free base, Ds is dilution factor for standard and P is percent purity of standard.

Employing the foregoing methods, patches hereinafter designated A, B, C, and D were prepared designed to deliver timolol base at rates of 31.7, 13.2, 6.7, and 0 (placebo) mcg/cm²/hr respectively. The actual in vitro delivery rates for the timolol containing patches determined as above described were 31.7 ($\pm$10.3%), 13.3 ($\pm$16.5%) and 8.6 ($\pm$2.7%) mcg/cm²/hr.

B. Clinical Evaluation

Clinical evaluation was carried out on twelve human volunteers (subjects). In the study, four patches were placed in the deltoid region of the arms, two on each arm. The patches were held in place with commercially available medical grade polyurethane tape. In ten of the subjects, each of the four different patches were employed. In two of the subjects, one B (15 mcg/cm²/hr) patch and three placebo patches were employed.

The subjects were divided into two groups: one group wore the patch for 96 hours (4 days) and the other group wore the patch for 168 hours (7 days). At the end of 96 hours or 168 hours, the patches were removed and each patch analyzed for timolol content as an indication of timolol not delivered from the patches. The difference between the initial timolol content of the patch (determined by accurate weight determination of the ointment in each patch) and the timolol remaining was taken as an estimate of timolol delivered and employed to determine apparent rate of delivery (flux). For determining the timolol remaining at the site of application, the tape, the patch, and gauze wipings of the skin were combined and timolol extracted therefrom with chloroform and the timolol partitioned into 0.1N $H_2SO_4$ and determined by high pressure liquid chromatographic analysis at 294 nm against timolol standard according to standard methods. The skin at the time of removal of the patch was examined for erythema and scored employing the Draize method. (A visual scoring method, c.f. Rothman, S., "Physiology and Biochemistry of the Skin", p. 54, University of Chicago Press, 1954.)

Another observation was made 24 hours later. The results are seen in Tables I and II. It is seen that there is greater indication of erythema 24 hours after removal than at the time of removal and therefore in determining the rate for administering a therapeutically effective amount of timolol in a long term application without irritation, the determination must be made at twenty-four hours or some time after removal of the patch.

TABLE I

| | | | | 96 Hour Study | | | | | | |
|---|---|---|---|---|---|---|---|---|---|---|
| | Flux | | | Draize Scores | | | | | | |
| | (Estimated) | | | 96 Hour | | | | 96 + 24 Hour | | |
| Sub- | (mcg/cm2/hr) | | | Reading | | | | Reading | | |
| ject | A | B | C | A | B | C | D | A | B | C | D |
| I | 24.4 | 15.8 | 16.3 | 1 | 1 | 1 | 0 | 3 | 1 | 0 | 0 |
| II | 20.3 | 12.6 | 4.1 | 0 | 0 | 2 | 1 | 0 | 0 | 0 | 0 |
| III | 19.9 | 12.5 | 3.0 | 0 | 0 | 0 | 0 | 3 | 3 | 2 | 0 |
| IV | 28.4 | 8.3 | 4.3 | 0 | 0 | 1 | 0 | 2 | 2 | 0 | 0 |

TABLE I-continued

| | 96 Hour Study | | | | | | | | | |
|---|---|---|---|---|---|---|---|---|---|---|
| | Flux (Estimated) (mcg/cm2/hr) | | | Draize Scores | | | | | | |
| | | | | 96 Hour Reading | | | | 96 + 24 Hour Reading | | |
| Subject | A | B | C | A | B | C | D | A | B | C | D |
| V | 31.6 | 19.9 | 19.2 | 0 | 0 | 1 | 0 | 1 | 1 | 1 | trace |
| VI | — | 18.8 | — | 0* | 1.5 | 1* | 1 | 1.5* | 2.5 | 0.5* | 0.5 |

*Asterisks indicate placebo scores. Subject VI had 1 timolol (Patch B) and 3 placebo patches (A, C, D) applied.

TABLE II

| | 168 Hour Study | | | | | | | | | |
|---|---|---|---|---|---|---|---|---|---|---|
| | Flux (Estimated) (mcg/cm2/hr) | | | Draize Scores | | | | | | |
| | | | | 168 Hour Reading | | | | 168 + 24 Hour Reading | | |
| Subject | A | B | C | A | B | C | D | A | B | C | D |
| VII | 19.2 | 14.3 | 9.7 | 0 | 0 | 0 | 1 | 1.5 | 1 | 1.5 | 1 |
| VIII | 28.8 | 18.4 | 8.0 | 1 | 1 | 0 | 0 | 2 | 2 | 1 | 0 |
| IX | 29.9 | 27.7 | 5.9 | 1 | 1 | 0 | 1 | 1 | 2.5 | 0.5 | 0.5 |
| X | 21.6 | 13.0 | 9.4 | 1 | 1 | 1.5 | 1 | 0 | 1 | 0 | 0 |
| XI | 27.7 | 11.9 | 8.1 | 1 | 0 | 1 | 1 | 2 | 2.5 | 2 | 1 |
| XII | — | 12.2 | — | 0* | 0 | 0* | 0 | 0* | 1.5 | 1* | 1 |

*Asterisks indicate placebo scores. Subject XII had 1 timolol (B) and 3 placebo patches (A, C, D) applied).

EXAMPLE II

A similar study was carried out with patches contructed to have a delivery rate of 12 mcg/cm$^2$/hr and in two sizes, 10 cm$^2$ and 16 cm$^2$ with an additional difference that after the fabrication of the patch, polyisobutylene/mineral oil (40/60) adhesive layer 3.5 mil thick was applied to the membrane surface.

The drug reservoir for Patch A, a 16 cm$^2$ drug bearing patch consisted of timolol hemihydrate in gelled mineral oil (25 percent w/w as free base in the 5 percent polyethylene in heavy mineral oil). The drug reservoir for Patch B, a 10 cm$^2$ drug bearing patch consisted of timolol hemihydrate in gelled mineral oil (12 percent w/w as free base). Placebo patches, C (16 cm$^2$) and D (10 cm$^2$) were prepared also. The membrane employed was microporous polypropylene of porosity 38 percent and thickness of 0.02 centimeter (Celgard 4 ply 2400) for a theoretical release rate of 11.25 mcg/cm$^2$/hr. The actual in vitro release rate was determined using the U.S.P. Paddle Method described in Example I.

Clinical studies were carried out on twelve human subjects. On the first day of the study, 16 cm$^2$ patches of types A and C were placed on the arms of subjects. On the fifth day (after 96 hours) 10 cm$^2$ patches of types B and D or two D type patches were placed on the arms, also in the deltoid region. The initial patches were retained in place. On the seventh day, seven days from the start of the study (168 hours) and three days (72 hours) from the time of attachment of the 10 cm$^2$ patch, the patches were removed. The in vivo release rate (flux) was determined in a manner described in Example I and the arms of the subjects were examined at the time of removal and 24 hours after removal and scored by the Draize method as described in Example I. The results are seen in Table II.

In addition to the study of wearability and skin flux, efficacy determinations were also carried out by making periodic determinations of reduction in exercise heart rate by bicycle ergometry. Those subjects who did not show a 25 percent reduction at 96 hours were given the 10 cm$^2$ patch Also others, randomly selected were given 10 cm$^2$ patches The results (percent reduction in exercise heart rate) at 168 hours are included in the table together with the maximum probable daily dose calculated as follows:

Flux × Surface Area of Patch × 24 hours.

The results show effective reduction of exercise heart rate.

| Subject | Flux in vivo mcg/cm$^2$/hr | Time (hrs) | Draize Scores 168 hours | Draize Scores 168 + 24 hours | Heart Rate Reduction (%) | Max[1] Daily Dose mg |
|---|---|---|---|---|---|---|
| 1 | 11.5 | 168 | 0 | 2 | 25 | 7.8 |
|   | 7.4 | 72 | 1 | 1.5 | | |
| 2 | 17.7 | 168 | 0 | 0 | 20 | 9.4 |
|   | 10.8 | 72 | 1 | 0 | | |
| 3 | 8.3 | 168 | 0 | 2 | 26 | 5.4 |
|   | 9.2 | 72 | 1 | 0 | | |
| 4 | 11.7 | 168 | 0 | 0 | 21 | 4.5* |
|   | — | 72 | — | — | | |
| 5 | 11.7 | 168 | 0 | 0 | 25 | 6.9 |
|   | 10.4 | 72 | 1 | 0 | | |
| 6 | 7.8 | 168 | 1 | 2 | 19 | 5.3 |
|   | 9.6 | 72 | 1 | 0 | | |
| 7 | 9.4 | 168 | 1 | 0 | 31 | 3.6* |
|   | — | 72 | — | — | | |
| 8 | 8.3 | 168 | 1 | 0 | 33 | 5.3 |
|   | 9.2 | 72 | 0 | 0 | | |
| 9 | 8.1 | 168 | 1 | 1 | 27 | 5.5 |
|   | 5.8 | 72 | 0 | 0 | | |
| 10 | 10.9 | 168 | 0 | 1.5 | 28 | 4.2* |
|   | — | 72 | — | — | | |
| 11 | 10.7 | 168 | 0.5 | 1 | 29 | 4.1* |
|   | — | 72 | — | — | | |
| 12 | 8.1 | 168 | 1 | 0 | 17 | 5.7 |
|   | 10.8 | 72 | 0 | 0 | | |

[1] The maximum daily dose is based on the sum of the timolol received by the subject from the 16 cm$^2$ and 10 cm$^2$ patches.
*Indicates that these subjects did not require a second patch at 96 hrs.

EXAMPLE III In vitro permeation of timolol through various adhesive and adhesive combination with auxiliary membrane as rate controlling member were measured by applying 40 percent timolol hemihydrate in gelled mineral oil on a backing material and layered with an adhesive film with or without a microporous membrane material.

The adhesive films were prepared by mixing together an appropriate polymer with mineral oil, casting the mixture onto a silicone release paper and drying to obtain a film of the desired thickness. The compositions of the films were as follows:

Film A
  49% low molecular weight polyisobutylene (av. M.W. 10,500 by the Staudinger method)
  21% high molecular weight polyisobutylene (av. M.W. 125,000 by the Staudinger method) 30% mineral oil Film B
  75% high molecular weight polyisobutylene 25% mineral oil Film C 60% high molecular weight polyisobutylene 40% mineral oil The auxiliary membrane, when employed, was microporous polypropylene of 38 percent porosity and thickness of 0.0025 centimeter.

The results were as follows:

| Film | Auxiliary Membrane | Film Thickness | Timolol Flow mcg/cm²/hr |
|---|---|---|---|
| A | No | 0.058 cm. | 47 |
| B | No | 0.075 cm. | 30 |
| C | Yes | 0.080 cm. | 24 |
| B | Yes | 0.100 cm. | 25 |

The results show that timolol flow can be controll by employing an appropriate adhesive as a membrane and also by employing an adhesive in combination with a microporous membrane. The foregoing microporous polypropylene auxiliary membrane was previously found to release timolol from a similar reservoir at a rate of 80 mcg/cm²/hr.

EXAMPLE IV

A rate controlling membrane providing suitable delivery rate for timolol therapy may be prepared from B film of Example III and Celgard 2402 film (38 percent porosity and 0.05 centimeter thickness and having a flux of 40 mcg/cm²/hr). A membrane so prepared would have a theoretical flux as determined by the series resistance equation of 17.1 mcg/cm²/hr.

$$\frac{1}{J_{net}} = \frac{1}{J_1} + \frac{1}{J_2}$$
$$= \frac{1}{40} + \frac{1}{30}$$
$$J_{net} = 17.1$$

EXAMPLE IV

A transdermal patch is prepared by coating with the aid of heat a composition of a polyester occlusive film with a mixture of 40 percent timolol, 40 percent mineral oil and 20 percent high molecular weight polyisobutylene, allowing the coating to solidify and then applying to the surface thereof first a polyurethane film and thereafter an adhesive film-forming composition 75 percent polyisobutylene and 25 percent mineral oil, drying and thereafter cutting to the desired 20 cm² size.

What is claimed is:

1. A method of administering a therapeutically effective amount of timolo transdermally over an extended period with minimal or no irritation to the skin comprising delivering timolo to the dermal surface at a zero order rate of from about 7 to no greater than about 20 micrograms per square centimeter per hour, wherein said timolol is delivered from a transdermal delivery system comprising a drug reservoir containing timolol dispersed in a gelled mineral oil semi-solid carrier said reservoir adhesive to an occlusive backing member and enclosed in a rate-controlling member wherein said rate-controlling member is selected from (1) a microproous membrane, (2) a diffusion rate-controlling membrane, (3) a rate-controlling adhesive layer and (4) a combination of microporous or diffusion rate-controlling membrane and rate-controlling adhesive layer.

2. A method according to claim 1 which comprises delivering timolol to the dermal surface at a zero order rate of from about 7 to about 15 micrograms per square centimeter per hour.

3. A method according to claim 2 wherein the rate for delivering timolol to the dermal surface is about 12 micrograms per square centimeter per hour.

4. A method according to claim 1 wherein the timolol is delivered to the dermal surface through a microporous membrane.

5. A method according to claim 1 wherein timolol is delivered to the dermal surface through a diffusion rate controlling membrane.

6. A method according to claim 1 wherein timolol is delivered to the dermal surface through a rate controlling adhesive layer.

7. A method according to claim 1 wherein timolol is delivered to the dermal surface through a combination of a membrane and a rate controlling adhesive layer.

8. A method for administering timolol transdermally for effective $\beta$-blockade with minimal irritation to the skin for an extended period of time which comprises delivering timolol to the dermal surface at a zero order rate of from about 7 to 15 micrograms per square centimeter per hour, wherein said timolol is delivered from a transdermal delivery system comprising a drug reservoir containing timolol dispersed in a gelled mineral oil semi-solid carrier, said reservoir adhered to an occlusive backing member and enclosed in a rate-controlling member, wherein said rate-controlling member is selected from (1) a microporous membrane, (2) a diffusion rate-controlling membrane, (3) a rate-controlling adhesive layer and (4) a combination of microporous or diffusion rate-controlling membrane and rate-controlling adhesive layer.

9. A transdermal delivery system suitable for administering timolol for an extended period with little or no irritation to the dermal surface which comprises:
(a) a backing member, said backing member being substantially impermeable to the drug,
(b) a drug reservoir member, contiguous to and substantially coextensive with one face of said backing member and consisting essentially of timolol dispersed in a semisolid carrier, and
(c) a rate controlling member superposed on the drug reservoir member and substantially coextensive therewith, said member controlling the flow of timolol from the reservoir to the skin surface of a zero order rate of from about 7 to no greater than 20 micrograms per square centimeter per hour, wherein said delivery system is prepared by
(i) selecting a drug reservoir composition and a specific polymeric membrane or combination of membrane and adhesive as the rate controlling member,
(ii) measuring the rate of release J of a drug reservoir composition through the selected rate controlling member or members into an isotonic phosphate buffer and
(iii) determining for the selected membrane or membrane and adhesive, optimal parameters to provided the desired flux J, where J is described by the equation $$J = \frac{E \cdot D \cdot Kp \cdot C_s}{h}$$

wherein E is membrane porosity if the rate controlling member in a microporous membrane or is unity if the rate controlling member is a diffusion rate controlling membrane, D is diffusion coefficient of drug through the reservoir or of reservoir carrier medium in the micropores of a porous membrane, or of drug through a diffusion rate controlling membrane, $K_p$ is partition coefficient of drug membrane and reservoir, or between medium in the micropores and reservoir, $C_s$ is drug concentration in the reservoir, h is membrane or rate controlling member thickness, and wherein the optimal parameters are calculated by varying the porosity E and/or the thickness h of said membrane or membrane and adhesive.

10. A delivery system according to claim 9 wherein the carrier for the drug is a gelled mineral oil.

11. A delivery system according to claim 9 wherein the rate controlling member is a membrane.

12. A delivery system according to claim 9 wherein the membrane is of laminated multilayers and wherein the overall rate J net is determined by the relationship $$\frac{1}{J_{net}} = \frac{1}{J_1} + \frac{1}{J_2} + \cdots$$

13. A delivery system according to claim 11 wherein the membrane is of microporous polypropylene.

14. A delivery system according to claim 11 wherein the membrane is of ethylene vinyl acetate.

15. A delivery system according to claim 11 wherein the membrane is of silicone.

16. A delivery system according to claim 11 wherein the membrane is of polyurethane.

17. A transdermal patch suitable for administering timolol for an extended period which comprises (a) a backing member of a material substantially impermeable to timolol; (b) a drug reservoir member adjacent to and coextensive with one face of said backing member, said drug reservoir member consisting essentially of timolol and a semi-solid gelled mineral oil carrier therefor, (c) a rate controlling member superposed on the drug reservoir member, said rate controlling member comprising at least one layer of a microporous membrane; and (d) an adhesive layer for affixing to the skin of a patient, wherein said patch delivers timolol at a zero order rate of from 7 to no greater than 20 micrograms per square centimeter per hour.

18. A patch according to claim 17 wherein the carrier in the drug reservoir is gelled mineral oil and the microporous membrane of the rate controlling member is microporous polypropylene.

19. A patch according to claim 17 wherein the carrier in the drug reservoir member is gelled mineral oil and the rate controlling member is a film of polyisobutylene and mineral oil.

20. A patch according to claim 17 wherein the carrier in the drug reservoir member is gelled mineral oil and the rate controlling member is a combination of (a) a film of polyisobutylene and mineral oil and (b) microporous polypropylene membrane.

* * * * *

UNITED STATES PATENT AND TRADEMARK OFFICE
CERTIFICATE OF CORRECTION

PATENT NO. : 4,752,478

DATED : June 21, 1988

INVENTOR(S) : Joseph V. Bondi, et al

It is certified that error appears in the above-identified patent and that said Letters Patent is hereby corrected as shown below:

Claim 1, line 52 and line 54, "timolo" should be --timolol--.

Signed and Sealed this

Twenty-second Day of November, 1988

Attest:

DONALD J. QUIGG

Attesting Officer

Commissioner of Patents and Trademarks